United States Patent [19]

Holzner et al.

[11] Patent Number: 5,508,259

[45] Date of Patent: Apr. 16, 1996

[54] PERFUMING COMPOSITION

[75] Inventors: Günter Holzner, Grand-Lancy; Paul Andersson, Troinex, both of Switzerland

[73] Assignee: Firmenich SA, Geneva, Switzerland

[21] Appl. No.: 353,570

[22] Filed: Dec. 9, 1994

Related U.S. Application Data

[63] Continuation-in-part of Ser. No. 178,690, Jan. 10, 1994, abandoned.

[30] Foreign Application Priority Data

Feb. 11, 1993 [CH] Switzerland ............................ 420/93

[51] Int. Cl.⁶ ............................................................ A61K 7/46
[52] U.S. Cl. .......................... 512/4; 512/3; 252/174.11; 424/65
[58] Field of Search ....................... 512/4, 3; 252/174.11; 424/65

[56] References Cited

U.S. PATENT DOCUMENTS

| | | | |
|---|---|---|---|
| 4,668,430 | 5/1987 | Schmolka | 512/1 |
| 4,803,195 | 2/1989 | Holzner | 512/4 |
| 4,818,522 | 4/1989 | Ferentchak et al. | 424/5 |
| 5,135,747 | 8/1992 | Faryniarz et al. | 512/4 |
| 5,194,262 | 3/1993 | Goldberg et al. | 424/65 |
| 5,258,174 | 11/1993 | Schebece | 424/65 |

FOREIGN PATENT DOCUMENTS 384034 12/1989 Switzerland ............................ 512/4

*Primary Examiner*—James H. Reamer
*Attorney, Agent, or Firm*—Pennie & Edmonds

[57] ABSTRACT

Non-aqueous perfuming composition intended for use in perfumed articles and devices, comprising at least two perfuming elements, wherein each of said perfuming elements has an olfactive character distinct from that of the others, and wherein one of said perfuming elements is in liquid form and the others in water-soluble microencapsulated form.

The perfuming composition according to the instant invention makes it possible to suppress body malodors through topical application thereof on the human body skin and provides advantageous olfactive effects when used for perfuming soaps and powder detergents.

20 Claims, No Drawings

PERFUMING COMPOSITION

CROSS REFERENCE

This is a continuation-in-part of U.S. application Ser. No. 08/178,690, filed Jan. 10, 1994, now abandoned.

BRIEF SUMMARY OF THE INVENTION

The instant invention relates to the perfumery and cosmetic industries. In particular, it provides a non-aqueous perfuming composition intended for use in perfumed articles and devices, comprising at least two perfuming elements, wherein each of said perfuming elements has an olfactive character distinct from that of the others, and wherein one of said perfuming elements is in liquid form and the others in water-soluble microencapsulated form.

This invention further relates to a method for suppressing body malodors, which comprises treating the skin of the human body through topical application of a perfuming composition as mentioned above.

Another object of the invention is to provide a method for improving the sensory impact of a perfumed product, which comprises incorporating therein a fragrance effective amount of a perfuming composition as mentioned above.

The invention further concerns a variety of perfumed consumer products containing this perfuming composition.

BACKGROUND OF THE INVENTION

U.S. Pat. No. 4,803,195, belonging to the same patentee, describes a perfuming composition having deodorant or antiperspirant activity and whose first advantage resides in the fact that it makes it possible to control the activation and diffusion of the perfume in time. The contents of the cited patent are hereby included by reference. This patent indicates how, thanks to the particular choice of the ingredients present in the composition, namely of the film-forming substrates and of the emulsifiers, it is possible to achieve reversible "reencapsulation" of the active deodorant ingredients, such that several successive activations can take place on the skin, without any need for further applications by the user. Thus, reencapsulation takes place in situ during the drying of the skin which follows a perspiration period.

European patent application EP 384 034-A2 describes a similar composition wherein, however, it was indicated that the use of polyvinylpyrrolidone as the film-forming component made it possible to obtain perfectly transparent alcoholic compositions, particularly useful in applications such as sticks and roll-ons, for which it was also desired to fulfill esthetical requirements. The contents of the cited application are also hereby included by reference.

U.S. Pat. No. 4,818,522 describes a malodor-reducing composition in which a water-immiscible adjuvant, which can be a fragrance, is encapsulated in an antiperspirant active material, said material providing slow release of the encapsulated adjuvant when in contact with moisture. This composition also provides protection of the encapsulated adjuvant during storage.

U.S. Pat. No. 5,135,747 discloses a malodor-reducing composition for body-care, which includes an unscented malodor counteractant mixture encapsulated within a semipermeable wall, a non-encapsulated fragrant perfume mixture and a cosmetically acceptable vehicle. The encapsulated, unscented deoperfume, slowly releases its malodor counteractant agent over a period of time, while the fragrant perfume provides a sensory impression.

Finally, European patent application EP 480 520 describes underarm hygiene products containing perfumes encapsulated in a filmforming encapsulation material which is capable of re-encapsulating the perfume in an allegedly more efficient manner than the encapsulation materials disclosed in U.S. Pat. No. 4,803,195.

These prior art perfuming compositions have two points in common: they are all intended for use in deodorant or antiperspirant products for body-care and, irrespective of their efficiency, they only allow the use of a perfume at a time, which is moreover the current practice in individual perfuming.

However, this practice meets with an inconvenient. The diffusion of the volatile emanations of a perfume, during a more or less prolonged amount of time, generally engenders a phenomenon of adaptation and olfactive saturation, causing on the observer a marked desensitization towards the currently used perfuming agents.

THE INVENTION

The present invention is based on the observation that sequential and automatic renewal of the nature of the active perfuming agents, as perceived by the user or by the observer, could effidently avoid olfactive desensitization.

Thus the invention provides a non-aqueous perfuming composition intended for use in perfumed articles and devices, comprising at least two perfuming elements, wherein each of said perfuming elements has an olfactive character distinct from that of the others, and wherein one of said perfuming elements is in liquid form and the others in water-soluble microencapsulated form.

According to a preferred embodiment of the invention, the composition comprises two perfuming elements, one being in liquid form and the other in water-soluble microencapsulated form.

By perfuming element, it is understood here any active odoriferous ingredient or any perfuming base or mixture of two or more active odoriferous ingredients of current use in perfumery. These ingredients can belong to distinct chemical classes including for example esters, ethers, alcohols, aldehydes, ketones, acetals, nitriles, terpenic hydrocarbons, nitrogen- or sulphur- containing heterocyclic compounds. They can be of synthetic origin or consist of essential oils of natural origin. Any known perfuming ingredient can in fact be used and typical examples of such odoriferous ingredients or perfuming compounds can be found in the literature. In this connection, textbooks such as that of S. Arctander, Perfume and Flavor Chemicals, Montdair, N.J., USA (1969) and that of P. Bedoukian, Perfumery and Flavoring Synthetics, Elsevier Publ. Co. (1967) may be cited.

Generally, each of said perfuming elements will consist of a mixture of several odoriferous ingredients, either in isolation, or, optionally, in a solution or suspension in solvents and adjuvants of current use. The choice of these perfuming ingredients will depend solely on the perfuming effect required, the nature of the article or product to be perfumed and the sensory impression that one desires to achieve. Since according to the invention each of the perfuming elements possesses a fragrance character which is distinct from that of the other perfuming element or elements, the choice of perfuming ingredients for each of the elements will also comply with this requirement.

The advantages of using the composition of the invention are quite obvious whenever the water-soluble microencapsulated element or elements of the perfuming composition is formed according to the teaching of U.S. Pat. No. 4,803,195. In fact, upon the use of a film-forming solid substrate such as polyvinyl acetate, polyvinyl alcohol, dextrines, natural or modified starch, vegetable gums, pectins, xanthanes, alginates, carragenans or yet cellulose derivatives such as for example carboxymethyl cellulose, methylcellulose or hydroxyethylcellulose, in combination with an emulsifying agent and a mixture of perfuming ingredients, there can be obtained perfuming compositions that, after microencapsulation, either separately in a reactor or in situ on the skin, become active through solubilisation once put into contact with a source of humidity, in particular perspiration. Such an activation engenders the release of the fragrant volatiles which had up until then been contained inside the microcapsules, which volatiles, according to the present invention either cover or replace those developed by the liquid element, to which the observer had been exposed from the first application of the perfuming composition and therefore developed a certain degree of adaptation.

The observer is thus subjected to a new odor impulse of different nature, which causes reactivation of his olfactive response and has the effect of prolonging the effectiveness of the composition.

The microencapsulated element or elements may be prepared not only in situ on the skin itself of the user, by means of the composition defined in U.S. 4,803,195, but also and mostly according to conventional microencapsulation techniques, which are perfectly well documented in the prior art [see for example: Spray Drying Handbook, $3^{rd}$ ed., K. Masters; John Wiley (1979)] and currently applied in the food industry or in the flavor and perfume industry. As a solid carrier, there are used hydrosoluble materials of varied nature, similar to those above-mentioned for the in situ microencapsulation. These are therefore in particular carbohydrates and vegetable gums, whose emulsion with the active perfuming ingredients or essential oils in the presence of an emulsifying agent is treated in current spray drying reactors. The microencapsulation can also be carried out by coacervation, the carrier being in this case formed of gelatine, or by prior polymerisation of urea with formaldehyde.

Like the liquid element of the perfuming base, the active odoriferous agents entrapped, and consequently stabilised, in the matrix of the microcapsules solid support, can be of varied nature.

According to the invention, the perfuming elements of the composition are of distinct olfactive nature and the only combination criterium resides in the hedonic and harmonious effect developed by them. In a preferred embodiment of the composition which comprises two perfuming elements, one of said elements is of a heavier odor character than the other. Thus, an element which develops a fresh, light, cologne or citrus type odor may harmonize well with an element having a heavier odor character, musky, amber-like or woody. As a result, it could be suggested to combine the first of these elements in liquid form with the second in microencapsulated form. The user would then be exposed to a first impression of freshness which would be followed, upon the activation resulting from rupture of the microcapsules during perspiration, or simply from contact with a source of humidity, by the release of heavier notes, such as musky or amber-like for example. On the other hand, it is well-known that a good number of perfuming ingredients are capable of antimicrobial activity. Such ingredients could then be preferably chosen, so that the purely perfuming action might be accompanied by the deodorant action related to their antimicrobial properties. In addition, antiperspirant agents, or even bacteride agents with disinfectant or germicide activity, can also be added, as well as bacteriostatic agents. By way of example, one can rite to this effect hexachlorophene, dichlorophenol, trichlorosalicylanilide (Anobial), tribromosalicylanilide (TBS), tetrachlorosalicylanilide (TCSA) and trichlorocarbanilide (TCC).

Antiperspirant agents include preferably aluminum salts, for example aluminum chlorohydrate. Other antiperspirant bases are described in the specialized literature [see for example: Herbert P. Fiedler, Der Schweiss, Edition Kantor KG, Aulendorf i. Württ, Germany].

As indicated above, the olfactive nature of the two perfuming elements present in the composition can be freely chosen. As a further example, one can also envisage the use according to the invention of a perfuming composition comprising a liquid element with a floral, fern or chypre character, combined with a microencapsulated element developing a fresh character of the orange blossom type, or say minty type.

The man in the art knows by experience that it is impossible to predict all the manners of realizing the invention leading to a precise definition of the perfuming compositions that can thus be created. This applies both to the definition of the ingredients and to the determination of their relative proportions. Consequently, the examples provided further on are given purely for the sake of illustration of particular embodiments and should not be interpreted in a restrictive manner.

According to a particular embodiment, the perfuming composition of the invention is characterized in that the two perfuming elements contain equivalent global ponderal amounts of active odoriferous ingredients. Thus, for example, concentrations of the order of 0.1 to 0.5% by weight of each of these two elements can be used in current applications namely for perfuming antiperspirant sprays or sticks. These are of course only indicative values, such proportions varying as a function of the nature of the article that one wants to perfume or of the particular olfactive effect one desires to achieve.

In the preparation of the encapsulated element, the proportion of perfume can vary between 1 and 35% of the total solid composition, or even more, depending on the support materials used.

The composition according to the invention can be conveniently used in deodorant or antiperspirant articles or devices. It is in practice a simple system which does not require application of special equipment for its use. Any conventional system of current use in cosmetics, and namely for applying deodorisers or antiperspirants, is convenient for application of the invention's composition. To this end, one can mention creams, sticks, roll-ons, smooth-ons, aerosols or yet powders.

In these applications, the above-mentioned embodiment of the perfuming composition wherein the micro-encapsulated perfuming element is of a heavier odor character than the liquid perfuming element, turns out to be particularly advantageous for the reasons already mentioned. It is clear, however, that other combinations of odor characters can be used. For example, one could imagine the use of a relatively tenaceous perfuming element of a powdery, oriental, character, in liquid form, combined with a micro-encapsulated element of a fresh, citrus or lavender odor, which would provide a fresh, sporty olfactive impulse following a surge of perspiration. As previously mentioned, the combination of two distinct olfactive characters is almost limitless.

When used in this type of applications the perfuming composition of the invention will also generally contain active deodorant or antiperspirant bases, or yet bactericidal or antimicrobial bases, in combination with the perfuming elements. Alternatively, or in addition, one of said perfuming elements may be formed of fragrant ingredients which are also capable of deodorant, bactericidal or antimicrobial activity. Such ingredients have become currently known in recent years and the skilled person finds no difficulty nowadays in composing the desired perfuming mixtures with such properties.

The perfuming composition according to the present invention is also quite advantageous for perfuming soaps and powder detergents.

It has in fact been discovered that the odor impact of this type of consumer products is greatly enhanced when they are perfumed with the composition of the invention. As a result of the presence in the latter of at s least two perfuming elements of distinct odor character, one in free form and at least one in microencapsulated form, the user is exposed to a fresh odor impression upon their use, since their odor will change upon contact with the water, by virtue of the rupturing of the capsules containing a distinct fragrance element.

The effect is very striking with soaps for example. When the soap is dry, it essentially develops the odor characteristic of the liquid perfuming element of the composition. This can typically be a rich, relatively heavy type of fragrance, for example, with a musky, floral character. Upon use, when the soap is humidified, the perfume or perfumes contained in the capsules are liberated. Now, these will generally be chosen to develop light, fresh notes, very volatile, for example minty, citrusy or fruity-type fragrances, typically associated with freshness and cleanliness. These very volatile notes generally form the headnote fraction of the classical perfume compositions, but they are not stable in the soap during a long storage or even just during the life time of use of the soap. After a while, they can no longer be perceived by the user and only the heavier part of the composition lingers on. The odor of the soap thus becomes heavy and dull, lusterless. Thanks to the composition according to the present invention, this no longer happens, since every time that the soap is put into contact with water the user is exposed to this impression of freshness, as if the soap had been just newly bought. On the other hand, the microencapsulation of the volatile, headnote-type fragrances, also provides for a more balanced odor of the soap. In fact, in the classically perfumed soaps, containing just one type of perfuming element, the latter fragrances tend to dominate the sensory impression perceived by the user, at least when the soap is freshly bought, totally masking the richer and warmer odor characters at the beginning of the use of the soap.

The same type of improvement was observed when the composition of the invention was used for perfuming powder detergents, as is apparent from the examples presented further on.

The perfuming composition of the invention is therefore quite advantageous for perfuming the various consumer products cited above and its use provides a method for improving the sensory impression imparted upon the user by such perfumed products.

Other advantages and embodiments of the invention are described in detail in the examples presented hereinafter.

EXAMPLE 1

A microencapsulated composition for use in body antiperspirants was prepared by means of the following ingredients (parts by weight):

|   |   | a) % | b) % | Origin |
|---|---|---|---|---|
| I | WATER | 49.0 | 49.0 |   |
|   | GLUCIDEX 21 (Maltodextrine DE 20–35) | 36.0 | — | ROQUETTES FRERES |
|   | NADEX (Maltodextrine DE 9–12) | 4.0 | — | GRAIN PROCESSING CORP. |
|   | SODIUM ALGINATE | 0.8 | 0.3 |   |
|   | CAPSUL (modified corn starch) | — | 40.5 | NATIONAL STARCH |
| II | TWEEN 20 (POE sorbitanmono-laurate) | 0.2 | 0.2 | ICI |
|   | PERFUME (SURF 635.040 E) | 10.0 | 10.0 | FIRMENICH |
|   |   | 100.0 | 100.0 |   |

After prior separate mixing, the two parts I and II were mixed together, part II having been added to part I, and the whole was homogenized by means of a Silverson type fast stirrer. The mixture was then spray dried in a CCM Sulzer apparatus with an emulsion output of 50 Kg/h, drying air: 320 m$^3$/h at 350° C. and 0.45 bar. There was thus obtained a fine powder, the diameter of the particles being comprised between 20 and 80 μm and the content in perfume being 20% by weight. This composition was used in the preparation of the following antiperspirant compositions.

Antiperspirant composition for smooth-ons

The composition was prepared by means of the following ingredients (parts by weight):

|   |   | % | Origin |
|---|---|---|---|
| I | CETYL ALCOHOL | 9.0 |   |
|   | BEESWAX | 4.5 |   |
|   | STEARIC ACID | 4.5 |   |
|   | FINSOLV TN (C12–C15 alcohol benzoate) | 10.0 | FINETEX |
|   | ARLACEL 165 (Glycerylstearate + PEG 1000 stearate) | 5.4 | ICI |
| II | ALUMINUM HYDROXYCHLORIDE in micronised powder | 20.0 |   |
|   | TALC | 5.0 |   |
| III | VOLATILE SILICONE OIL (Cyclomethicone) | 38.1 |   |
| IV | PERFUME (microencapsulated) a) or b) (see above) | 3.0 |   |
|   | PERFUME (liquid) FOUGERE 66.450 | 0.5 | FIRMENICH |
|   |   | 100.0 |   |

Part I was heated until complete melting at 80° C. and parts II, BI, and IV were added successively to the melt under vigorous stirring. After cooling to 40°–50° C., the whole was poured into smooth-on type containers.

Antiperspirant composition for sticks

An antiperspirant composition for dry sticks was prepared by means of the following ingredients (parts by weight):

|   |   | % | Origin |
|---|---|---|---|
| I | OCTADECANOL | 19.0 |   |
|   | ARLACEL 165 (Glycerylstearate + PEG 1000 stearate) | 1.0 | ICI |
|   | PEG 1000 | 5.0 |   |

-continued

|   |                                                        | %    | Origin    |
|---|--------------------------------------------------------|------|-----------|
| II | AEROSIL 200<br>(colloidal SiO$_2$)                    | 1.4  | DEGUSSA   |
|   | TALC                                                   | 1.0  |           |
|   | REZAL 36 P<br>(Complex zirconium chlorhydrate)        | 19.0 | REHEIS    |
|   | PERFUME (microencapsulated)<br>a) or b) (see above)   | 3.0  |           |
| III | DOW CORNING FLUID 345<br>(Cyclomethicone)           | 50.0 |           |
| IV | PERFUME (liquid)                                      | 0.6  | FIRMENICH |
|   | FOUGERE 66.450                                         |      |           |
|   |                                                        | 100.0 |          |

Part I was heated to 90° C. until complete dissolving of all the ingredients; then, once the heating had been stopped, part II was added to the obtained mixture. Parts III and IV were successively added under stirring and the whole was poured into appropriate moulds at about 65° C.

Suspension for roll-on antiperspirants

An antiperspirant composition for roll-ons was prepared by means of the following ingredients (parts by weight):

|   |                                                                      | %     | Origin       |
|---|----------------------------------------------------------------------|-------|--------------|
| A | BENTONE GEL IPM<br>(Isopropyl myristate &<br>stearalkonium hectorite &<br>propylene carbonate) | 16.00 | NL IND.      |
|   | DOW CORNING SILICONE<br>FLUID 344 (Cyclomethicone)                   | 30.25 | DOW CORNING  |
|   | HOSTAPHAT KL 340 N<br>(Trilaureth - 4 phosphate)                     | 4.00  | HOECHST      |
|   | REZAL 36 GP<br>(Aluminium zirconium<br>tetrachlorohydrex gly)        | 20.00 | REHEIS       |
|   | HERCULES EHEC (X-high)<br>(Ethyl hydroxyethylcellulose)              | 1.00  | HERCULES     |
|   | FINSOLV TN<br>(C12–C15 alcohol benzoate)                             | 25.00 | FINETEX      |
|   | PERFUME (microencapsulated)<br>a) or b) (see above)                  | 3.00  |              |
|   | PERFUME (liquid)                                                     | 0.75  | FIRMENICH    |
|   | FOUGERE 66.450                                                        |       |              |
|   |                                                                      | 100.00 |             |

The silicone oil, the emulsifier, the liquid perfume and the Bentone gel were mixed by means of a turbine [A], while separately the cellulose was dispersed in the Finsolv until a gel [B] was obtained.

The two mixtures [A] and [B] were mixed together, the Rezal was added thereto under stirring.

The microencapsulated perfume was finally poured with caution into the obtained mixture.

Antiperspirant spray for aerosol

|   |                                                | %    | Origin        |
|---|------------------------------------------------|------|---------------|
| A | VOLATILE SILICONE OIL<br>(Cyclomethicone)     | 50.4 | DOW CORNING   |
|   | PERFUME (liquid, VERA 75.308)                  | 1.8  | FIRMENICH     |
|   | BENTONE GEL IPM<br>(Quaternium 18 hectorite)  | 4.0  | NL INDUSTRIES |
|   | PARAFFIN OIL 30–40 cP                          | 6.0  |               |
| B | AACH<br>(Activated Al—Cl hydrate)              | 33.0 | REHEIS        |
| C | PERFUME (microencapsulated)<br>a) or b) (see above) | 4.8 |         |
|   |                                                | 100.0 |              |

The ingredients of part A were admixed until obtaining a thick mass, then part B was added thereto. The whole was mixed for a few minutes by means of an Ultra Turrax turbine before carefully adding thereto part C. The obtained suspension was poured into aerosol containers to which there was added the propellent. The latter was a 90:10 mixture of isobutane and propane (Drivosol 27) used in a proportion of 70% for 30% of suspension.

EXAMPLE 2

A microencapsulated composition A for use in a soap was prepared by means of the following ingredients (parts by weight):

|   |                                          | a) %  | b) %  | Origin                  |
|---|------------------------------------------|-------|-------|-------------------------|
| I | WATER                                    | 49.0  | 49.0  |                         |
|   | GLUCIDEX 21<br>(Maltodextrine DE 20–35) | 33.5  | —     | ROQUETTES FRERES        |
|   | NADEX<br>(Maltodextrine DE 9–12)        | 4.0   | —     | GRAIN PROCESSING CORP.  |
|   | SODIUM ALGINATE                          | 0.8   | 0.3   |                         |
|   | CAPSUL<br>(modified corn starch)        | —     | 38.0  | NATIONAL STARCH         |
| II | TWEEN 20<br>(POE sorbitanmono-laurate)  | 0.2   | 0.2   | ICI                     |
|   | PERFUME<br>(GOLDEN 147.034)             | 12.5  | 12.5  | FIRMENICH               |
|   |                                          | 100.0 | 100.0 |                         |

After prior separate mixing, the two parts I and II were mixed together, part II having been added to part I, and the whole was homogenized by means of a Silverson type fast stirrer.

The mixture was then spray dried in a CCM Sulzer apparatus with an emulsion output of 50 Kg/h, drying air: 320 m$^3$/h at 350° C. and 0.45 bar.

There was thus obtained a fine powder, the diameter of the particles being comprised between 20 and 80 /gm and the content in perfume being 25% by weight.

A second composition B was prepared identically but using a perfume of the type FLEUR DE MENTHE 68.733 (origin: Firmenich)

These compositions were then used for preparing a perfumed soap I starting from a standard alcaline soap base, composed of tallow, lard and coconut oil (origin: Unichema, Holland), by admixture of the following ingredients:

| SOAP I | |
|---|---|
| Ingredients | Parts by weight |
| Soap base | 97.6 |
| Liquid perfume*<br>(JUPITER 148.035) | 1.0 |
| Composition A | 0.8 |
| Composition B | 0.6 |
| Total | 100.0 |

*origin: Firmenich

The perfumes were incorporated into the soap base by means of a laboratory extruding machine of the BV6 type (origin: Stéphane Beck, Nyon, Switzerland). As a result of the mechanical stress applied during the extrusion and stamping of the soap, some of the capsules are smashed and therefore this freshly prepared soap develops an odor wherein the musky-floral notes typical of the liquid fragrance JUPITER are pleasantly combined with the more volatile apple type odor of the GOLDEN fragrance and the minty notes of the FLEUR DE MENTHE. When the soap was evaluated by a panel of five expert individuals, they indicated that they perceived a very pleasant overall fragrance where all these characters were nicely harmonized.

The panel was then asked to use the soap and to comment on its odor, when wet.

They indicated that they perceived a very agreeable and sudden surge of a fresh, fruity and minty fragrance, providing a pleasant sensation of cleanliness. The latter abated shortly after ceasing the use of the soap, giving place to the balanced initial odor, but was repeatedly perceived every time the soap was re-used, and this over a period of two weeks. A strong fragrant impact was always perceived upon washing the hands with the soap.

A blind test was then carried out by the same panel of five individuals with this same soap I and two other soaps II and III, perfumed by means of a mixture of the three fragrances cited above, present in the soap in the same relative proportions, i.e., 1% of JUPITER, 0.2% of GOLDEN and 0.15% of FLEUR DB MBNTHE. Soap II contained this mixture in liquid form and soap III contained a certain amount of this mixture in liquid form and a slightly higher amount in microencapsulated form. The panel was asked to qualify the odor of the three soaps, both dry and wet, and to indicate their preference.

The results of this blind test are summarized below.

| CONDITIONS | SOAP I | SOAP II | SOAP III |
|---|---|---|---|
| Freshly prepared dry soap | Pleasant, well-balanced floral-musky, fruity and minty odor. | Strong headnote wherein the minty note is over-dominant and masks the rest. | Same as II, but the odor is not as strong. |
| Freshly prepared wet soap | Sudden burst of a fresh and strong fruity-minty, volatile fragrance, quality of the odor clearly changed from above, nice clean sensation, strong impact. | No change from above. | Sudden, much stronger odor perception, but no change in quality; headnote still over-dominated by minty character. |
| Wet soap two weeks later | Still the same impression of freshness and cleanliness, the sudden change in the quality of the odor perceived as compared to the dry soap. Same impact as above. | Dull, heavy odor, wherein the minty note has been replaced by a much heavier musky type character, devoid of freshness. | Same as above. The intensity of the odor is clearly enhanced upon wetting, but there is no perception of a refreshing change in quality. |

The panel was unanimous in its preference for soap I and its members indicated that they had a pleasant impression of freshness every time they washed their hands with this soap, without feeling that the minty, fruity character was overpowering, unlike what happened for example with soap Ill. In fact, globally they had the impression that soap I was much more pleasantly perfumed than for example soap Ill.

These results indicated that although the overall perfuming composition had exactly the same composition in the three soaps, as regards the perfuming ingredients present and their relative proportions, the olfactive effect provided was entirely different with soap I, as compared to soaps II and III, as a result of the fact that in soap I the three perfuming elements provided an altering perfuming impulse between the dry and wet soap, resulting in a much stronger odor impact.

The same type of effect was observed when soap I was prepared with a microencapsulated mixture of GOLDEN 147.034 and FLEUR DE MENTHE 68.733, in the same relative proportions as above, i.e. with these two perfumes admixed before being encapsulated.

EXAMPLE 3

A microencapsulated perfuming composition C was prepared in a similar manner to that described in example 2, but using as perfume a fragrance of the type HAWAI 148.036 (origin: Firmenich). With this composition there was prepared a perfumed powder detergent I, using a base consisting of spray-dried detergent beads (origin: Henkel, Germany) and the following ingredients:

| Detergent I | |
|---|---|
| Ingredients | Parts by weight |
| Detergent base | 79.65 |
| Sodium perborate | 20.00 |
| Perfuming composition C | 0.20 |
| Liquid perfume* | 0.15 |
| (JAPONIA 41516 B) | |
| Total | 100.0 |

*origin: Firmenich

The detergent had thus acquired a fresh, floral-musky odor imparted by the JAPONIA composition. The characteristic fruity odor of the HAWAI composition, generally very volatile and diffusive, could not be perceived. Two other detergent samples were prepared by admixing the following ingredients:

| Detergent II | | Detergent III | |
|---|---|---|---|
| Ingredients | % | Ingredients | % |
| Detergent base | 79.80 | Detergent base | 79.80 |
| Sodium perborate | 20.00 | Sodium perborate | 20.00 |
| Liquid perfume (JAPONIA 41516 B) | 0.15 | Liquid perfume[a] | 0.10 |
| | | Encapsulated perfume[a] | 0.10 |
| Liquid perfume (HAWAI 148.036) | 0.05 | | |
| Total | 100.0 | | 100.0 |

[a] Mixture of JAPONIA 41516 B and HAWAI 148.036 so as to provide 0.15% of the first and 0.05% of the second in the soap.

a) Mixture of JAPONIA 41516 B and HAWAI 148.036 so as to provide 0.15% of the first and 0.05% of the second in the soap.

After a month of storage at 40° C., in packages similar to commercial ones, the three detergents were then submitted for evaluation to a panel of experts, on a blind test. The panel was asked to comment on the odor of the detergents in powder form, as well as when dissolved in water at 40° C., and to indicate their preference.

The results of this test are summarized hereinbelow.

|  | DETERGENT I | DETERGENT II | DETERGENT III |
| --- | --- | --- | --- |
| Dry powder | weakly floral-musky odor. | same as I, together with a weak fruity note. | very similar to II, but even weaker odor. |
| Powder dissolved in water at 40° C. | fresh and strong fruity odor, clearly perceptible, strong impact. | very weak odor as above. | odor is only slightly stronger than above, the effect was almost imperceptible. |

The panel individuals were of the unanimous opinion that only with detergent I did they perceive the sudden change in odor which gave them the sudden impression of a much stronger fragrance when the powder was put in the water.

What is claimed is:

1. Non-aqueous perfuming composition intended for use in perfumed articles and devices, comprising at least two perfuming elements, at least one of which is present in liquid form and at least one other of which is in a water-soluble microencapsulated form, with the odor character of said perfuming element or elements in microencapsulated form being sufficiently distinct from the odor character of the liquid perfuming element to generate upon an observer prior exposed to the fragrance of the liquid perfuming element or elements an odor impulse of different nature when the microencapsulated perfuming element or elements are solubilized.

2. Perfuming composition according to claim 1, wherein one perfuming element imparts a relatively light odor character, while the other perfuming element provides a heavier odor character.

3. Perfuming composition according to claim 2, wherein the perfuming element that provides a heavier odor character is in the microencapsulated form.

4. Perfuming composition according to claim 2, wherein said two perfuming elements contain equivalent global ponderal amounts of active odoriferous ingredients.

5. Perfuming composition according to claim 4, wherein the proportion of active ingredients present in each of said perfuming elements is between about 0.1 and 5.0% by weight, relative to the total weight of the composition.

6. Perfuming composition according to claim 1, wherein microencapsulation occurs after topical application of the composition.

7. Perfuming composition according to claim 1, containing an antimicrobial base in combination with the active perfuming elements.

8. Deodorant or antiperspirant device or article, intended for body care, containing a perfuming composition according to claim 1.

9. Deodorant or antiperspirant device or article according to claim 8, wherein the the liquid perfuming element imparts a relatively light odor character to the composition and the microencapsulated perfuming element imparts a heavier odor character.

10. Deodorant or antiperspirant device or article according to claim 8, chosen from the group consisting of creams, sticks, roll-ons, smooth-ons, aerosols or powders.

11. A soap or a powder detergent containing a perfuming composition according to claim 1.

12. A soap or detergent according to claim 11, wherein the microencapsulated perfuming element imparts a relatively light and fresh odor character to the composition and the liquid perfuming element provides a heavier odor character.

13. A method for suppressing body malodors, which comprises treating the skin of the human body through topical application of a perfuming composition according to claim 1.

14. A method for improving the sensory impact of a perfumed product which comprises incorporating therein a flagrance effective amount of a composition according to claim 1.

15. The method of claim 13 wherein the composition has a first odor character upon application to the skin and a second, distinct odor character after the microencapsulated perfuming element is solubilized by body fluids.

16. The method of claim 14 wherein the composition has a first odor character upon topical application to the skin of a human body and a second, distinct odor character after the microencapsulated perfuming element is solubilized by body fluids.

17. The composition according to claim 1 wherein the odor character of the microencapsulated perfuming element is distinct from the odor character of the liquid perfuming element both initially and after the microencapsulated perfuming element is solubilized.

18. Non-aqueous perfuming composition intended for use in perfumed articles and devices, comprising at least two perfuming elements, at least one of which is present in liquid form and at least one other of which is in a water-soluble microencapsulated form, wherein the composition has a first perceptible odor upon formulation, and a second perceptible odor of a different nature than the first odor after the microencapsulated perfuming element is solubilized.

19. The composition according to claim 17 wherein the first odor is imparted by the odor character of the liquid perfuming element, and the second odor is imparted by the solubilized microencapsulated perfuming element.

20. The composition according to claim 19 wherein the odor character of the solubilized microencapsulated perfume element is distinct from the odor character of the liquid perfuming element.

\* \* \* \* \*